(12) United States Patent
Reimels et al.

(10) Patent No.: US 12,004,964 B2
(45) Date of Patent: *Jun. 11, 2024

(54) EXPANDABLE INTERBODIES AND RELATED METHODS

(71) Applicant: Alphatec Spine, Inc., Carlsbad, CA (US)

(72) Inventors: William Reimels, Hamilton, OH (US); Max C. Zemezonak, San Diego, CA (US)

(73) Assignee: Alphatec Spine, Inc., Carlsbad, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/074,718

(22) Filed: Dec. 5, 2022

(65) Prior Publication Data

US 2023/0102897 A1 Mar. 30, 2023

Related U.S. Application Data

(63) Continuation of application No. 17/190,798, filed on Mar. 3, 2021, now Pat. No. 11,564,809.

(60) Provisional application No. 62/985,610, filed on Mar. 5, 2020, provisional application No. 63/062,663, filed on Aug. 7, 2020.

(51) Int. Cl.
*A61F 2/44* (2006.01)
*A61F 2/46* (2006.01)
*A61F 2/30* (2006.01)

(52) U.S. Cl.
CPC ............ *A61F 2/447* (2013.01); *A61F 2/4611* (2013.01); *A61F 2002/30156* (2013.01); *A61F 2002/30224* (2013.01); *A61F 2002/30433* (2013.01); *A61F 2002/30471* (2013.01); *A61F 2002/3054* (2013.01); *A61F 2002/30556* (2013.01); *A61F 2002/30579* (2013.01); *A61F 2002/30784* (2013.01); *A61F 2002/30971* (2013.01); *A61F 2002/4627* (2013.01)

(58) Field of Classification Search
CPC .................. A61F 2/447; A61F 2/4611; A61F 2002/30156; A61F 2002/30224; A61F 2002/30433; A61F 2002/30471; A61F 2002/3054; A61F 2002/30556; A61F 2002/30579; A61F 2002/30784; A61F 2002/30971; A61F 2002/4627
USPC ............................................ 623/17.11–17.16
See application file for complete search history.

(56) References Cited

U.S. PATENT DOCUMENTS 8,105,382 B2 1/2012 Olmos
8,382,842 B2 2/2013 Greenhalph
(Continued)

OTHER PUBLICATIONS

USPTO acting as International Searching Authority, "International Search Report and Written Opinion," for International Application No. PCT/2021/043419, dated Nov. 1, 2021.

*Primary Examiner* — Jessica Weiss
(74) *Attorney, Agent, or Firm* — Robert Winn

(57) ABSTRACT

The present disclosure relates to expandable interbodies that include superior and inferior shells and a control assembly positioned between and inside of the shells, the control assembly including nested cages operably connected to each other with an adjustment screw. Rotation of the adjustment screw translates the cages relative to each other, which in turn causes the shells to open or expand.

19 Claims, 7 Drawing Sheets

(56) References Cited

U.S. PATENT DOCUMENTS

| | | | |
|---|---|---|---|
| 8,568,481 | B2 | 10/2013 | Olmos |
| 8,632,595 | B2 | 1/2014 | Weiman |
| 8,679,183 | B2 | 3/2014 | Glerum |
| 8,685,098 | B2 | 4/2014 | Glerum |
| 8,845,731 | B2 | 9/2014 | Weiman |
| 9,034,041 | B2 | 5/2015 | Wolters |
| 9,320,610 | B2 | 4/2016 | Alheidt |
| 9,370,434 | B2 | 6/2016 | Weiman |
| 9,492,288 | B2 | 11/2016 | Wagner |
| 9,566,168 | B2 | 2/2017 | Glerum |
| 9,585,766 | B2 | 3/2017 | Robinson |
| 9,585,767 | B2 | 3/2017 | Robinson |
| 9,717,601 | B2 | 8/2017 | Miller |
| 9,788,971 | B1 | 10/2017 | Stein |
| 9,801,733 | B2 | 10/2017 | Wolters |
| 9,907,673 | B2 | 3/2018 | Weiman |
| 9,962,270 | B2 | 5/2018 | Alheidt |
| 10,034,765 | B2 | 7/2018 | Blain |
| 10,034,769 | B2 | 7/2018 | Baynham |
| 10,098,759 | B2 | 10/2018 | Weiman |
| 10,111,758 | B2 | 10/2018 | Robinson |
| 10,137,009 | B2 | 11/2018 | Weiman |
| 10,166,117 | B1 | 1/2019 | Daffinson et al. |
| 10,278,830 | B1 | 5/2019 | Walker |
| 10,383,741 | B2 | 8/2019 | Butler |
| 10,426,632 | B2 | 10/2019 | Butler |
| 10,639,166 | B2 | 5/2020 | Weiman |
| 10,646,351 | B2 | 5/2020 | Blain |
| 10,709,575 | B2 | 7/2020 | Robinson |
| 10,779,957 | B2 | 9/2020 | Weiman |
| 10,898,344 | B2 | 1/2021 | Alheidt |
| 10,925,752 | B2 | 2/2021 | Weiman |
| 11,013,617 | B2 | 5/2021 | Weiman |
| 11,376,134 | B1 | 7/2022 | Dewey et al. |
| 2005/0043800 | A1* | 2/2005 | Paul ............ A61B 17/1757 623/17.13 |
| 2013/0274886 | A1* | 10/2013 | Matsumoto ........ A61F 2/442 623/17.16 |
| 2014/0236297 | A1* | 8/2014 | Iott ............... A61F 2/447 623/17.15 |
| 2015/0272743 | A1* | 10/2015 | Jimenez ........... A61F 2/447 623/17.16 |
| 2016/0081814 | A1 | 3/2016 | Baynham |
| 2016/0120660 | A1* | 5/2016 | Melkent .......... A61F 2/447 623/17.16 |
| 2017/0224505 | A1* | 8/2017 | Butler ............... A61F 2/44 |
| 2018/0344474 | A1* | 12/2018 | Hessler ......... A61F 2/30771 |
| 2019/0201209 | A1* | 7/2019 | Branch .......... A61F 2/4465 |

\* cited by examiner

EXPANDABLE INTERBODIES AND RELATED METHODS

RELATED APPLICATIONS

This application is a continuation of U.S. Non-provisional application Ser. No. 17/190,798, filed Mar. 3, 2021, which claims priority to U.S. Provisional Application Nos. 62/985,610, filed Mar. 5, 2020, and 63/062,663, filed Aug. 7, 2020, the entire contents of each of which are herein incorporated by reference.

BACKGROUND

The present disclosure relates to expandable implants such as spinal interbody and intervertebral body devices and, more particularly, to vertebral interbodies that are expandable after placement in the spine.

Fusion cages, as well as other types of interbodies and devices, are frequently utilized in spinal surgery inside a vertebra or in the disc space between respective vertebra (interbody). With interbody devices, one or more such spinal bodies are placed between vertebrae to provide support and promote fusion between adjacent vertebrae. Such fusion may be necessary because of disease, injury, general deterioration, or a congenital problem.

The goal of most spinal surgeries is to minimize the trauma of the surgery itself. One way to minimize the trauma is to create as small an access port as possible to reach the surgical site; however, a small access port then limits the size of the tools and implants that can pass through the access port.

A few interbody devices, however, are now being made that are expandable. Expandable interbodies are initially smaller than traditional non-expandable (static) interbodies such that the expandable interbodies may be more easily inserted and/or implanted into the disc space. The expandable interbodies, once positioned in the disc space, are expanded to a desirable size to achieve the amount of expansion necessary for the particular patient.

SUMMARY

The present disclosure relates to expandable interbodies that include superior and inferior shells and a control assembly positioned between and inside of the shells. The control assembly is configured to control the expansion or contraction of the shells. The superior shell has a proximal end and a distal end and defines a superior surface extending from the proximal end to the distal end configured to engage an inferior surface of a first vertebral body. The superior shell also has two side walls each wall having a proximally angled channel and a distally angled channel. The inferior shell has a proximal end and a distal end, the inferior shell defining an inferior surface configured to engage a superior surface of a second vertebral body. The inferior shell has two side walls each wall having a proximally angled channel and a distally angled channel. The control member includes interlocking proximal and distal cages and an adjustment screw defining a longitudinal axis. The adjustment screw is configured to engage with the proximal and distal cages. The proximal cage comprises a pair of superior lateral projections and a pair of inferior lateral projections respectively configured to engage with the pairs of proximally angled channels of the superior and inferior shells. Similarly, the distal cage has a pair of superior lateral projections and a pair of inferior lateral projections respectively configured to engage with the pairs of distally angled channels of the superior and inferior shells. Rotation of the adjustment screw causes the distal cage to move longitudinally relative to the proximal cage, which in turn causes the interbody to expand or contract in a direction transverse to the longitudinal axis.

The superior and inferior shells may include distal and proximal angled surfaces, and the distal and proximal cages also include superior and inferior angled surfaces that engage with the angled surfaces of the superior and inferior shells. At least one of the angled surfaces of the proximal and distal cages may define a rounded surface or cylindrical-shaped surface so as to achieve a linear point of contact between it and the corresponding angled surface of the superior and/or inferior shell. The cylindrical-shaped surface may be a pin, which may be a distinct material from that of the cage to which it is secured or a part of. The material of the pin may be selected to achieve a lower coefficient of friction between it and the ramps of the superior and/or inferior shells than would be achieved if the material of the pin were identical to that of the cage.

The adjustment screw of the control assembly may be threadingly engaged to the distal cage and may be in a fixed longitudinal orientation relative to the proximal cage. The adjustment screw may threadingly engage with the proximal cage and may be in a fixed longitudinal orientation relative to the distal cage. The adjustment screw may threadingly engage with both the proximal cage and the distal cage.

The relative movement between the distal and proximal cages may be translated to the superior and inferior cages by the force applied by the angled surfaces of the proximal and distal cages on the angled surfaces of the superior and inferior shells. The relative movement between the distal and proximal cages may be translated to the superior and inferior cages by the interaction between the lateral projections and lateral channels.

At least one of the superior and inferior shells may be curved at the distal end of the interbody. The superior and inferior shells may be curved toward each other at their respective distal ends so as to form a bullet-like nose shape that at least partially encloses the distal end of the interbody when in a collapsed configuration.

When in an expanded configuration, the superior shell, inferior shell, proximal cage, and distal cage may each include openings therethrough extending from the superior surface of the superior shell to the inferior surface of the inferior shell so as to define a channel for bone growth.

The interbodies disclosed herein may include at least some titanium alloy or may be comprised entirely of titanium alloy. At least one of the superior shell, inferior shell, proximal cage, distal cage, and adjustment screw may include a porous material. The porous material may be comprised of layers of porous sheets that have been diffusion-bonded to form a uniform material.

The superior surface of the superior shell and/or the inferior surface of the inferior shell may include a cutout or a depression containing a layer of a porous material, which material may be the result of a sintering process, an additive manufacturing process, or diffusion-bonding two or more porous sheets of material. The porous material may include titanium or another suitable metal or polymer.

The superior surface may define a first plane and the inferior surface may define a second plane that is substantially parallel to the first plane when the interbody is in a collapsed configuration. The first plane may be substantially parallel to the second plane when the interbody is in an expanded configuration. The first plane may be substantially not parallel to the second plane when the interbody is in an expanded configuration. The superior surface may define a first plane and the inferior surface may define a second plane, and the first and second planes may be substantially parallel to each when the interbody is collapsed and when it is expanded.

The superior and inferior shells may be designed to at least partially nest within each other when the interbody is in a collapsed configuration. The proximal and distal cages may be designed to contact respective inside surfaces of the side walls of the superior and inferior shells so as to provide structural support to the interbody. The edge of the side wall of either the superior shell or the inferior shell may include projections with the edge of the side wall of the other shell including depressions so as to receive the projections, which may provide the interbody with greater structural integrity when the interbody is in a collapsed configuration.

The proximal and distal cages may include one or more projections extending beyond the superior and/or inferior surfaces that may provide greater stability to the superior and/or inferior shell when the expandable interbody is in an expanded configuration. The lateral projections of the proximal and distal cages may extend through the superior and inferior surfaces when the interbody is in an expanded configuration.

Also disclosed herein are methods of implanting an expandable interbody as disclosed herein. Such methods include the steps of, with an inserter, positioning the interbody in a collapsed configuration in an intervertebral disc space, expanding the interbody by rotating a control handle on the inserter that in turn rotates the adjustment screw, and releasing the expanded interbody from the inserter. The method may further include, before releasing the expanded interbody from the inserter, injecting a material that promotes bone growth into the interbody through an opening in the proximal end of the interbody.

BRIEF DESCRIPTION OF THE DRAWINGS

The embodiments set forth in the drawings are illustrative and exemplary in nature and not intended to limit the subject matter defined by the claims. The following detailed description of the illustrative embodiments can be better understood when read in conjunction with the following drawings wherein like structure is indicated with like reference numerals and in which:

DETAILED DESCRIPTION

The present disclosure relates to expandable and/or dynamic interbody (between adjacent vertebrae), intravertebral-body (inside the vertebrae) and/or spinal stabilization devices that may or may not be used as interbody fusion cages or devices, interbody/intravertebral bodies/body stabilization devices and/or the like (collectively hereinafter, spinal device(s)) for providing support, stabilization and/or promoting bone growth between or inside vertebrae that have been destabilized or otherwise due to injury, illness and/or the like. Particularly, the present disclosure provides various versions of dynamic (expandable and/or expandable and retractable) interbody/intravertebral body devices that are usable in a spinal column of a human.

Figure 1:
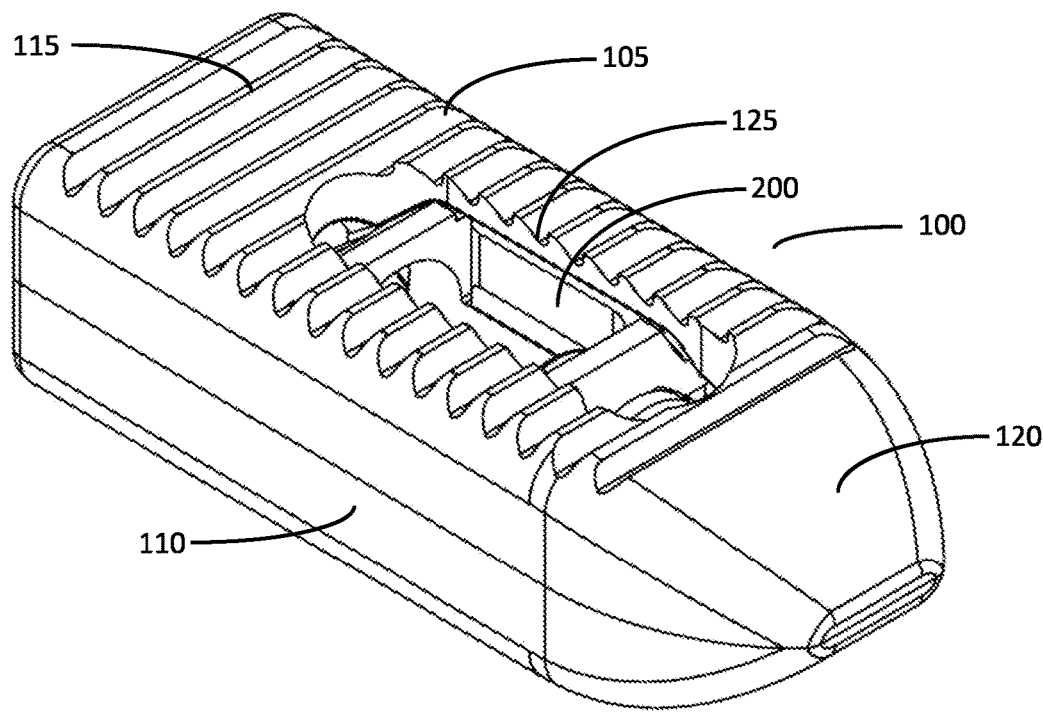
FIG. 1 is a perspective view showing an embodiment of an expandable interbody from a distal end of the interbody in a collapsed configuration.

FIG. 1 illustrates a representative dynamic spinal interbody device or expandable implant or interbody 100. FIG. 1 is a perspective view of interbody 100 from its distal end with interbody 100 in an unexpanded or collapsed state. Interbody 100 includes a superior shell 105 and an inferior shell 110. A superior surface of superior shell 105 is intended to contact and support an inferior surface of a first vertebral body. Similarly, an inferior surface of inferior shell 110 is intended to contact and be supported by a superior surface of a second vertebral body. In this illustrated embodiment, superior shell 105 and inferior shell 110 include ridges or teeth 115 configured to resist or minimize movement of interbody 100 after being placed in the intervertebral space between the first and second vertebrae. Some embodiments further or alternatively include a roughened surface that can be achieved with a coating and/or a surface treatment. The first and second vertebrae can represent, for example, L1-L2, L2-L3, L3-L4, L4-L5, or even L5-S1 of a human spine. Though interbody 10 could alternatively be used in the thoracic spine or even the cervical spine.

Interbody 100 has a distal end 120 comprised of the respective distal ends of superior shell 105 and inferior shell 110. Distal end 120 is shown as being tapered or shaped like the nose of a bullet. In some embodiments, the distal end of interbody 100 is not tapered at all, though tapering of the distal end can aid in the insertion of interbody 100 into the intervertebral disc space. In some embodiments, such tapering can consist of relatively straight but angled surfaces, and in some embodiments, such tapering can include one or more curves. Distal end 120 is illustrated as having substantially no ridges or teeth 115. In some embodiment, distal end 120 is completely smooth. In some embodiments, distal end 120 includes more ridges or teeth 115 than is illustrated in FIG. 1.

FIG. 1 illustrates that the edges of superior shell 105 and inferior shell 110, when in an unexpanded state, meet each other so as to form a closed shell that encloses a control assembly 200, which is discussed in greater detail below. Such a closed-shell configuration can increase the structural strength of interbody 100, which stability may be desired when implanting interbody 100 into a patient's intervertebral disc space. However, in some embodiments, such a closed-shell configuration may not be desirable, and superior shell 105 and inferior shell 110 may include one or more gaps between them even when interbody 100 is in a collapsed configuration. In some embodiments, superior shell 105 and inferior shell 110 are fully separated from each other when interbody 100 is in a collapsed configuration.

It is seen in FIG. 1 that superior shell 105 and inferior shell 110 each comprise both a horizontal surface and respective side walls. Although not shown, in some embodiments, the edges of the side walls can include projections and corresponding holes or slots for receiving the projections. For example, the inferior surface of the side walls of superior shell 105 can include one or more projections that are received, when in the unexpanded state, by corresponding holes in the superior surface of the side walls of inferior shell 110. Such a configuration can increase the structural integrity or stability of interbody 100 when in an unexpanded state, which can be particularly useful when interbody 100 is inserted into the intervertebral space and may be subject to compaction forces to be positioned correctly.

FIG. 1 also illustrates that superior shell 105 includes graft window 125. A similar graft window is found in inferior shell 110 as well as in control assembly 200. These graft windows allow for bone growth through interbody 100 after it has been implanted. In some embodiments, the graft window found in control mechanism is in substantial alignment with the graft windows of superior shell 105 and inferior shell 110 only when interbody 100 is in an expanded configuration. These graft windows also allow materials that induce or promote bone growth to be inserted or pushed into interbody 100 and at least partially flow out of interbody 100 to potentially contact and interact with the bony surfaces of the superior and inferior vertebral bodies. In some embodiments, interbody 100 includes only one or no graft windows. In some embodiments, interbody 100 includes three or more graft windows, which may be positioned on interbody 100 in locations other than those illustrated in FIG. 1. In some embodiments, interbody 100 includes a porous material through which bone-growth-promoting materials may pass. Such porous material may also allow for bone growth into interbody 100. In some embodiments, as is discussed in greater detail below, interbody 100 can achieve in-growth of new bone instead of or in addition to achieving through growth.

Figure 2:
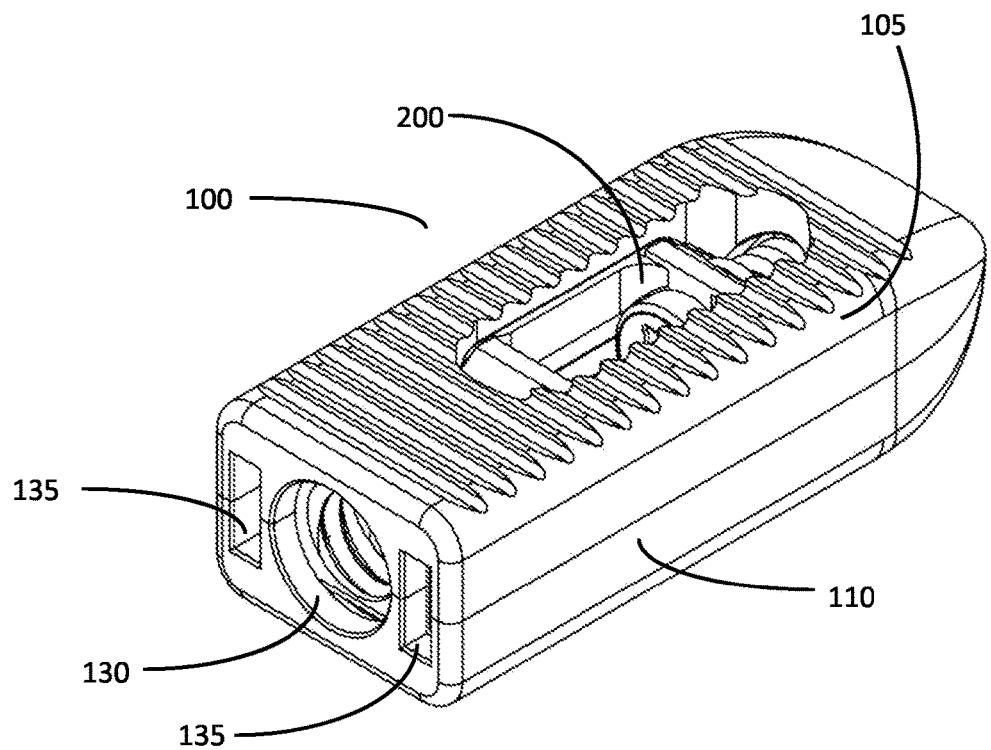
FIG. 2 is a perspective view of the embodiment of FIG. 1 from a proximal end of the interbody.

FIG. 2 is a rear perspective view of interbody 100 illustrating a proximal bore 130 formed by both superior shell 105 and inferior shell 110. Proximal bore 130 in conjunction with lateral slots 135 allow an inserter to be secured to interbody 110. Proximal bore 130 further allows the passage of bone-growth-promoting material into interbody 100 and potentially through its graft window(s). An inserter would further include an engagement portion that secures to a proximal end of control assembly 200, which is discussed in greater detail below. Lateral slots 135 prevent or resist rotation of interbody 100 during insertion and when interbody 100 is being secured to or released from the inserter.

Figure 3:
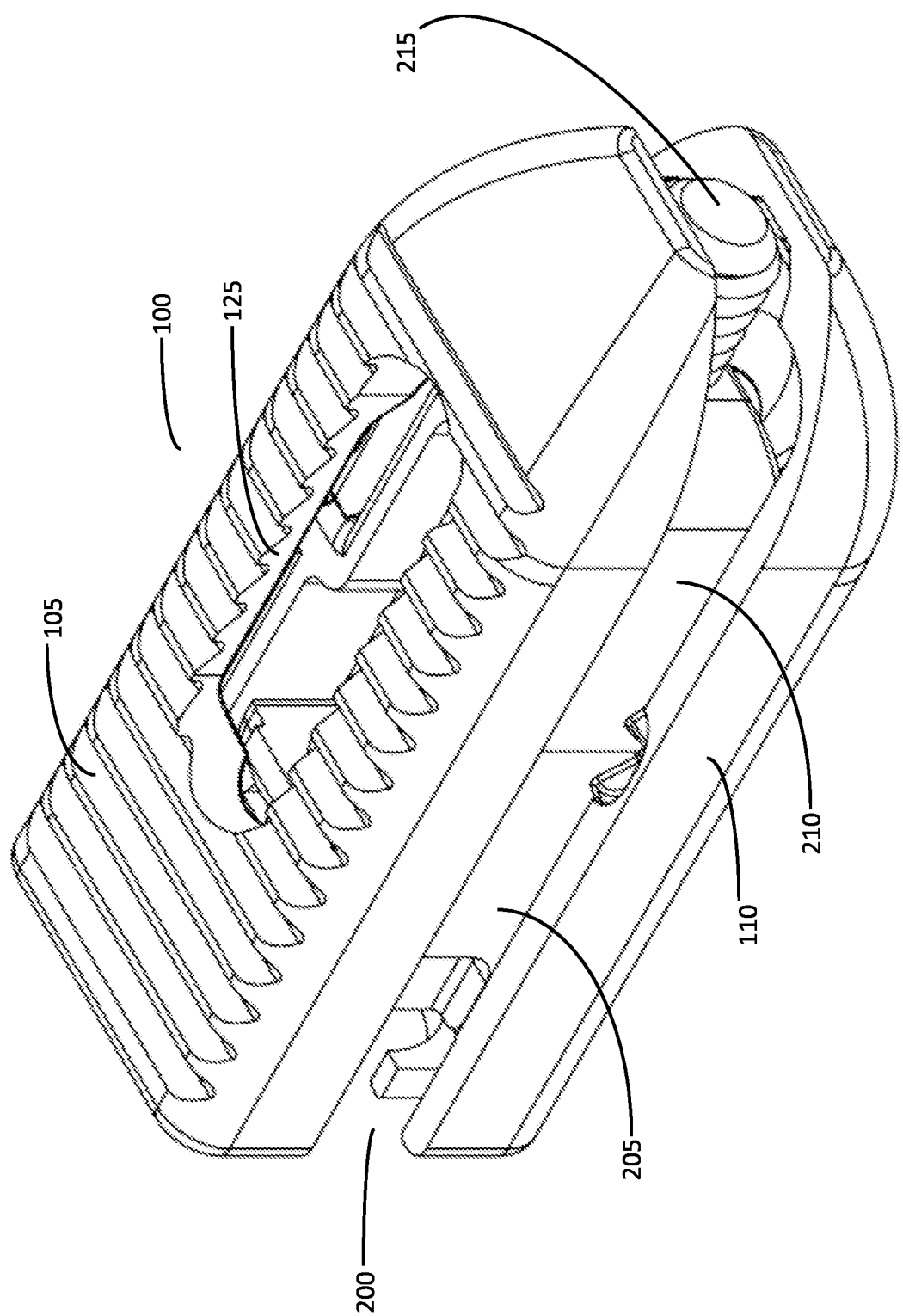
FIG. 3 is a perspective view of the embodiment of FIG. 1 from the distal end in an expanded configuration.

FIG. 3 illustrates interbody 100 in an expanded state in which superior shell 105 and inferior shell 110 have separated from each other in a relatively parallel fashion such that the superior surface of superior shell 105 and the inferior surface of inferior shell 110 remain substantially parallel to each other as interbody 100 is expanded. In some embodiments, the interaction between control assembly 200 and superior shell 105 and inferior shell 110 achieve an expansion of interbody 100 that results in the superior and inferior surfaces not being parallel when interbody 100 is fully expanded.

Expanding interbody 100 partially reveals control assembly 200 that is situated between and inside of superior shell 105 and inferior shell 110. Control assembly 200 includes a proximal cage 205, a distal cage 210, and an adjustment screw 215 (illustrated in FIG. 4). Proximal cage 205 and distal cage 210 are configured to interlock with each other—as illustrated in more detail in FIG. 4—so as to allow relative movement or translation between them along a longitudinal axis extending between the proximal and distal ends of interbody 100.

In the illustrated embodiment, expansion of interbody 100 from the unexpanded state to the expanded state is achieved when adjustment screw 215 is rotated so as to bring the proximal end of proximal cage 205 closer to the distal end of distal cage 210, essentially nesting the two cages more closely together. Movement of the cages applies a force to one or more interior surfaces of superior shell 105 and inferior shell 110 causing the two shells to separate as shown in FIG. 3.

In some embodiments, proximal cage 205 and distal cage 210 achieve expansion by moving away from each other. Such expansion achieved by essentially reversing the movement of proximal cage 205 and distal cage 210 is achieved by adjusting the channels found on superior shell 105 and inferior shell 110 (which channels are discussed in greater detail below).

Figure 8:
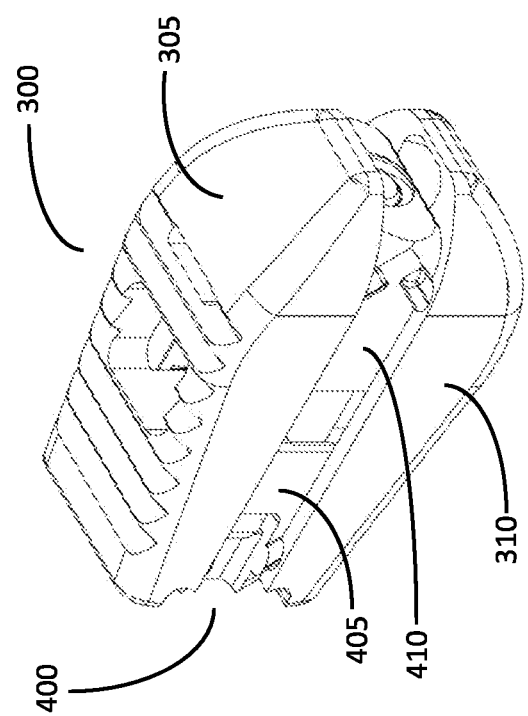
FIG. 8 is a perspective view of the embodiment of FIG. 7 from the distal end in an expanded configuration.

FIG. 2 illustrates that proximal cage 50 includes threaded bore 110 on its proximal end configured to threadingly receive an inserter as illustrated in FIG. 8. In some embodiments, the inserter engages interbody 10 with any number of other suitable engagement means, such as an inserter tube with one or more protruding lobes that insert into a similar keyed shaped hole that allows passage of the tube through the proximal cage and then partially rotate to secure the lobes to the inner wall.

Interbody 100 is illustrated as having a length that is greater than its width as well as its unexpanded and expanded height. In some embodiments, the width of interbody 100 is greater than illustrated and may even approach and/or exceed the length (or depth) of the interbody. The length (or depth) and/or width of interbody 100 is from about 5 mm to about 30 mm, from about 10 mm to about 25 mm, or from about 15 mm to about 20 mm. The unexpanded height of interbody 100 is from about 4 mm to about 20 mm, from about 6 mm to about 15 mm, or from about 7 mm to about 12, and the expanded height is from about 12 mm to about 30 mm, from about 15 mm to about 25 mm, or 17 mm to about 20 mm.

In some embodiments, interbody 100 is configured to one or more states of partial expansion. For example, where full expansion results in a height of 20 mm, some embodiments of interbody 100 will be configured to occupy a partial height of about 13 mm, about 15 mm, about 17 mm, or a value between those values. Interbody 100 will be designed to maintain these partial expansion values without collapsing under compressive forces. This can be achieved by using various means of resistance that restrict or limit the rotation of adjustment screw 215 or the movement of proximal cage 205 and/or distal cage 210 relative to superior shell 105 and/or inferior shell 210.

Figure 4:
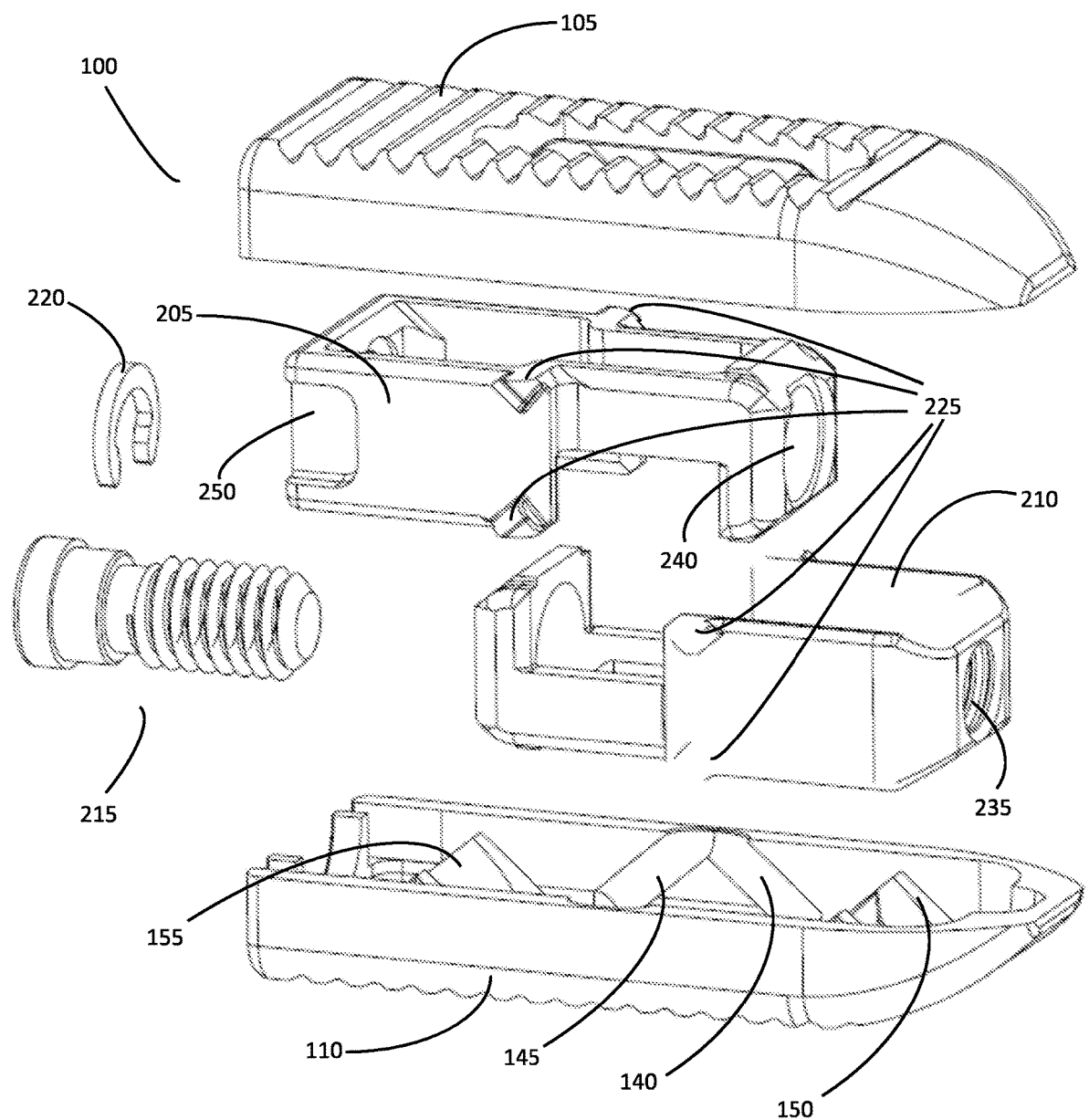
FIG. 4 is an exploded view of the embodiment of FIG. 1.

FIG. 4 is an exploded view of interbody 100 illustrating that, in this embodiment, control assembly 200 further includes a retention pin 220 that holds adjustment screw 215 in a fixed relationship relative to proximal cage 205. It will be understood, however, that adjustment screw 215 may be threadingly engaged with proximal cage 205 such that rotation of adjust screw 215 causes it to translate relative to proximal cage 205.

Adjustment screw 215 is inserted through a distal opening 240 of proximal cage 205 so that the threaded portion of adjustment screw 215 extends distally of proximal cage 205 at which point retention pin 220 is inserted into proximal cage 205 and at least partially around a collar portion of adjustment screw 215 thereby allowing adjustment screw 215 to rotate. In some embodiments, retention pin 220 provides a resistance force to the rotation of adjustment screw 215 so as to limit or prevent undesired rotation of adjustment screw 215.

In some embodiments, adjustment screw 215 is a twin screw comprising a distal and a proximal screw portion with the distal screw portion threadingly engaged within a threaded bore of the proximal screw. In other words, distal opening 240 may, in some cases, comprise a threaded bore. In some such embodiments, distal cage 210 does not have a threaded bore, but, instead includes features intended to engage with and/or secure a distal end of adjustment screw 215.

Retention pin 220 can comprise any number of suitable materials, such as a metal (e.g., steel, titanium, alloys thereof, etc.) or a polymer (polyvinylidene fluoride, polyethylene, polypropylene, polydimethylsiloxane, parylene, polyamide, polytetrafluoroethylene, polymethylmethacrylate, silicone, polyimide, PEEK, and polyurethane or a combination thereof). In some embodiments, retention pin 220 is internally threaded though in some embodiments, retention pin 220 is not internally threaded but simply applies a frictional force against adjustment screw 215.

The threaded portion of adjustment screw 215 that extends beyond proximal cage 205 threadingly engages a threaded distal opening 235 of distal cage 210 such that rotation of adjustment screw 215 causes distal cage 210 to move relative to proximal cage 205. In some embodiments, adjustment screw 215 is fixed relative to distal cage 210 and threadingly engages proximal cage 205. In some embodiments, adjustment screw 215 engages the respective proximal ends of the two cages rather than the respective distal ends of the two cages.

Figure 6:
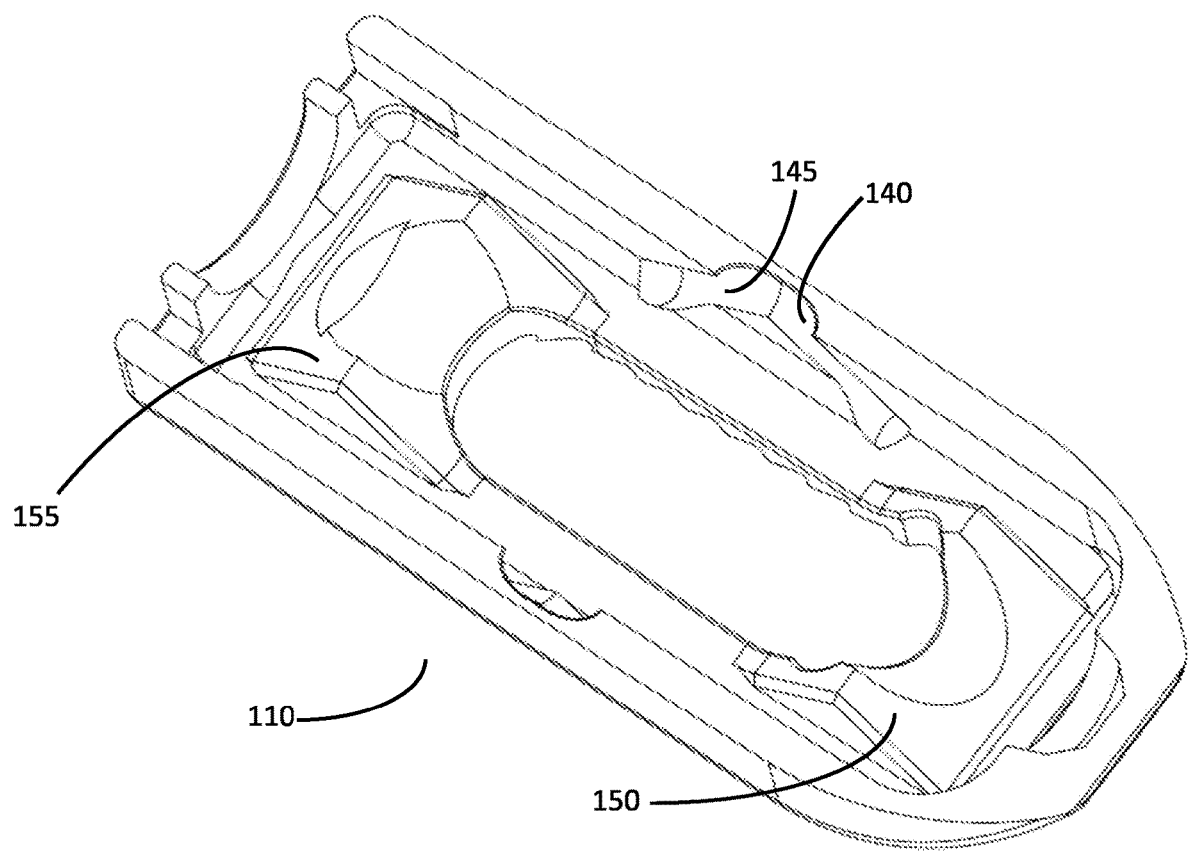
FIG. 6 is a perspective view of one of the two shells of the embodiment of FIG. 1.

FIGS. 4 and 6 illustrate that one side wall inferior shell 110 includes channels 140 and 145, one of which is distally angled (channel 140) and one of which is proximally angled (channel 145). The opposite side wall of inferior shell 110 includes channels that mirror channels 140 and 145. As will be understood by a skilled artisan, the position and angle of these channels may be adjusted to achieve different types of expansion of the interbody. For example, in some embodiments, the positions of the channels can be reversed so that the reverse translation of the cages is required to achieve expansion of the interbody.

A skilled artisan will appreciate that the channels discussed and illustrated herein may also be slots that extend through the shell from the interior surface to the exterior surface. A skilled artisan will also appreciate that although four channels are illustrated and discussed in each of the superior and inferior shells, similar outcomes may be achieved with fewer than four channels. For example, in some cases, the number of channels or slots on each of the superior and inferior shells is two.

Inferior shell 110 further includes distal ramps 150 and proximal ramps 155. Each set of ramps in this embodiment includes a proximal slope and a distal slope. Superior shell 105 contains similar channels and ramps. In some embodiments, superior shell 105 and inferior shell 110 are identical not only with respect to their overall shape but also to their interior and exterior surfaces. In some embodiments, only their interior surfaces are identical, and their exterior surfaces are distinct. Channels 140 and 145 are shown as depressions in inferior shell 110. In some embodiments, slots that pass through the shell may be used instead of channels.

Figure 5A:
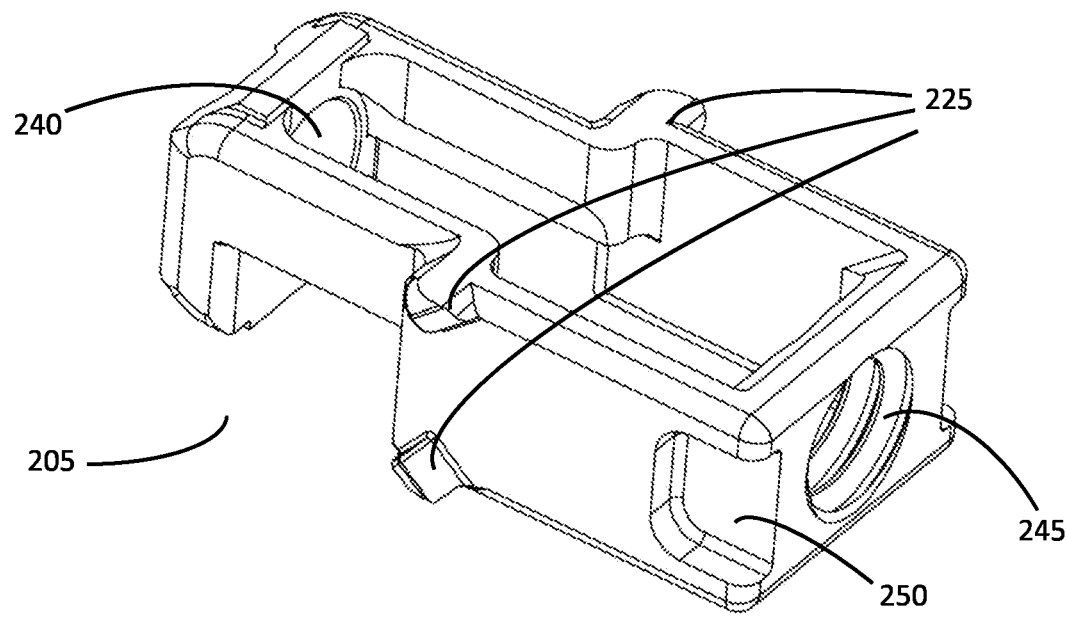
FIGS. 5A and 5B are perspective views of the cages illustrated in FIG. 4.
Figure 5B:
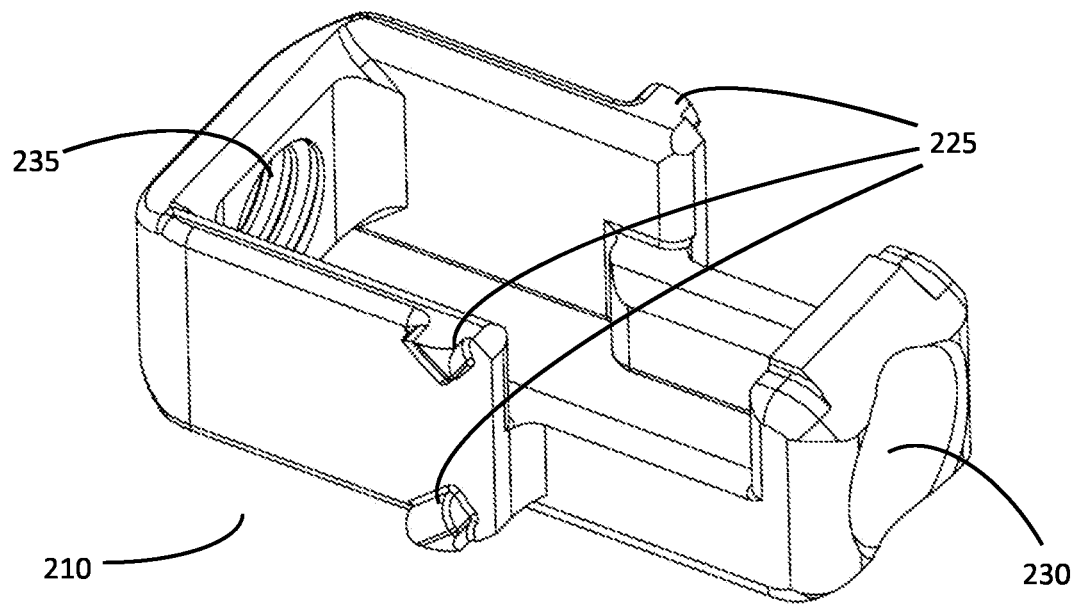

FIGS. 4, 5A, and 5B illustrate various aspects of proximal cage 205 and distal cage 210. Each cage in this illustrated embodiment has proximal and distal ends, each one of which includes an opening or bore hole that may or may not be threaded. Each cage in this embodiment also has side walls that are designed to allow proximal cage 205 and distal cage 210 to fit together and allow for translational movement between the two. Each cage also has four lateral extensions 225, two located superiorly and two located inferiorly. Superior lateral extensions 225 of proximal cage 205 are designed to fit in and slide along the proximally angled channels of superior shell 105, and superior lateral extensions 225 of distal cage 210 are designed to fit in and slide along the distally angled channels of superior shell 105. Inferior lateral extensions 225 of proximal cage 205 and distal cage 210 are similarly designed and configured to fit in and slide along the respective proximally and distally angled channels 145 and 140 of inferior shell 210. Longitudinal translation of proximal cage 205 and distal cage 210 causes their various lateral extensions 225 to slide along the angled channels and, in some embodiments, apply a force to the angled channels of superior shell 105 and inferior shell 110 to thereby cause the two shell pieces to separate.

FIGS. 4, 5A, and 5B also illustrate that proximal cage 205 and distal cage 210 each include ramped or angled surfaces at their respective distal and proximal ends. These ramped or angled surfaces are designed and configured to interact with the respective proximal and distal ramps found in superior shell 105 and inferior shell 110. Longitudinal translation of proximal cage 205 and distal cage 210 causes their various ramped surfaces to contact and, in some embodiments, apply a force to the ramped surfaces of superior shell 105 and inferior shell 110 to thereby cause the two shell pieces to separate. Contact between these various surfaces further serves to provide overall stability to interbody 100 as it is expanded and/or collapsed.

Figure 9:
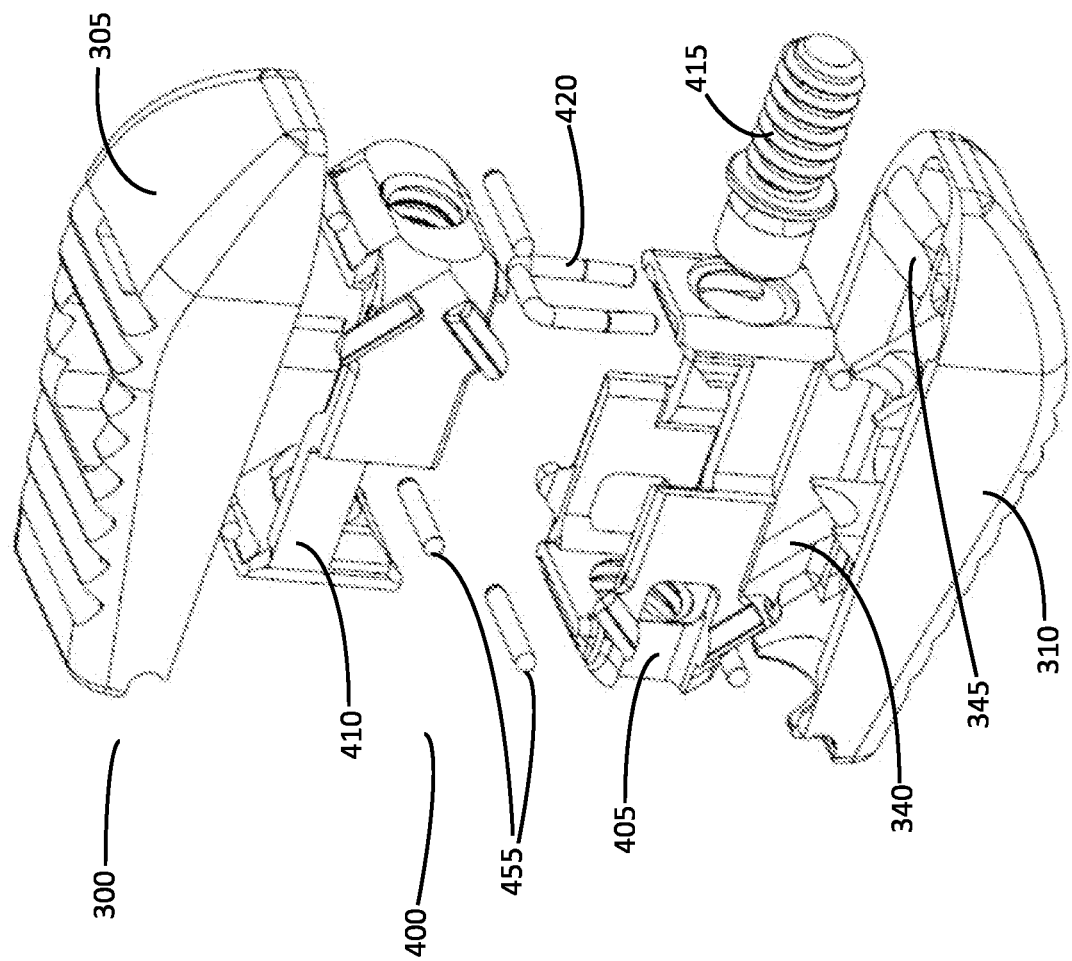
FIG. 9 is an exploded view of the embodiment of FIG. 7.

In some embodiments, one or more of the various ramped surfaces of proximal cage 205 and distal cage 210 includes or consists of a rounded surface or, in some embodiments, a pin or cylindrically shaped element that reduces the friction between the cages and the ramped surfaces of the two shells (see, for example, the embodiment illustrated in FIG. 9). In some embodiments where a pin or cylindrically shaped element is used, the material of such element may be selected to have a lower coefficient of friction than the material comprising the cages. In some embodiments, the surfaces of the pin or cylindrically shaped element are treated or prepared so as to exhibit a lower coefficient of friction.

Although not illustrated, a pin may also serve as lateral extension 225. In other words, one or more pins secured to proximal and/or distal cages 205 and 210 may extend at least partially on one lateral side or the other of interbody 100 so that the end of the pin(s) extends into one or more channels or slots on superior shell 105 and/or inferior shell 110.

FIGS. 4 and 5A also illustrate the indentions or cutouts 250 located on the proximal end of proximal cage 205. As will be illustrated in FIG. 10, such cutouts are configured to receive a portion of an insertion instrument so as to not only better secure the inserter to the interbody but also to prevent the interbody from rotating when the interbody is expanded.

FIG. 5A illustrates that proximal cage 205 includes a proximal bore 145 that is threaded. In this embodiment, threaded bore 145 is configured to receive an engagement member of an inserter, which engagement member threads into threaded bore 145. Once threadingly engaged, an expansion tool is able to pass through the engagement member so as to engage and rotate the proximal end of adjustment screw 215, which rotation of adjustment screw 215 causes displacement of distal cage 210 relative to proximal cage 205—because adjustment screw 215 is threadingly engaged with threaded bore 235 located at the distal end of distal cage 210 (illustrated in FIGS. 4 and 5B)—thereby causing interbody 100 to collapse or expand depending on which direction adjustment screw 215 is rotated.

In some embodiments, one or both of superior shell 105 and inferior shell 110 includes a porous material, which can be metallic or polymeric or a combination of the two. In some embodiments, one or both of superior shell 105 and inferior shell 110 include a cutout or depression in their exterior surface(s) to accommodate a layer of porous material that is configured to occupy the cutout or depression in the exterior surface(s). In some embodiments, the layer of porous material is simply affixed or secured to the superior and/or inferior surface of interbody 100, and no cutout is used or required. In some embodiments, the porous material is one or more layers of a porous sheet, such as one or more layers of a sheet of porous titanium. The layer(s) of porous titanium can be diffusion bonded to each other and to the exterior surface(s) of superior shell 105 and/or inferior shell 110. In some embodiments, the porous material surrounds, is adjacent to, or replaces one or both of the graft windows. In some embodiments, the porous material is positioned on one or more side walls in addition to or instead of on a superior or inferior surface of interbody 100.

The components illustrated in FIG. 4 can be formed of any suitable material, such as one or more metals or one or more polymers. Such materials include titanium, steel, cobalt, gold, platinum, silver, iridium, tantalum, tungsten, and alloys thereof, polyvinylidene fluoride, polyethylene, polypropylene, polydimethylsiloxane, parylene, polyamide, polytetrafluoroethylene, polymethylmethacrylate, polyimide, PEEK, and polyurethane. In some embodiments, one or more of the components illustrated in FIG. 4 includes a porous material. Porous materials can include porous metals as well as porous polymers or a mixture of the two. For example, in some embodiments, one or more components includes or is manufactured from porous titanium. In some embodiments, the porous titanium comprises layered sheets of porous titanium that have been diffusion bonded to each other to form a unitary whole. In some embodiments, one or more of superior shell 105, inferior shell 110, distal cage 210, or proximal cage 205 is manufactured from or includes layered sheets of porous titanium that have been diffusion bonded to each other. When such porous components are used, this allows for bone growth through and/or into interbody 100 itself rather than just through graft windows, if present.

Figure 7:
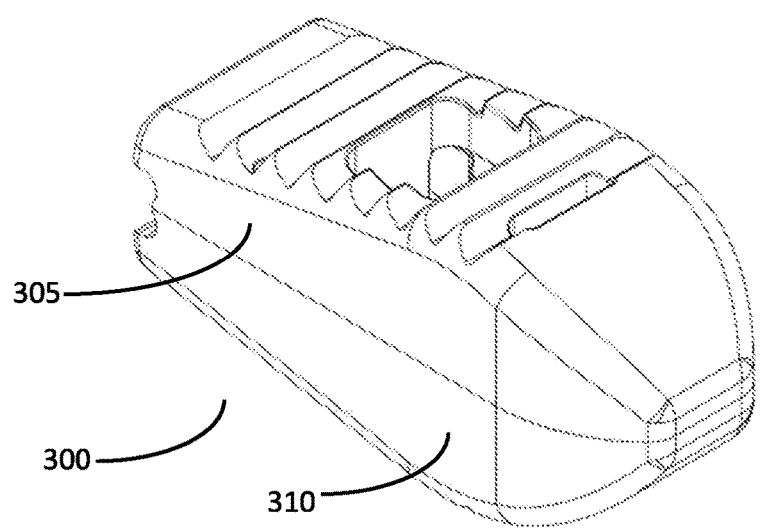
FIG. 7 is a perspective view showing another embodiment of an expandable interbody from a distal end of the interbody in a collapsed configuration.

FIG. 7 illustrates another embodiment of an expandable interbody 300 that operates much like interbody 100 discussed above; however, interbody 300 achieves a type of lordotic expansion. Interbody 300 has a superior shell 305 and inferior shell 310, each having a distal end and a proximal end. The distal ends of both shells are formed into a tapered end or bullet-shaped nose.

Superior shell 305 has a superior surface, and inferior shell 310 has an inferior surface. FIG. 7 illustrates that the superior and inferior surfaces of the shells are not parallel when interbody 300 is in a collapsed configuration. FIG. 8 illustrates interbody 300 in an expanded configuration. In this embodiment, the angle between the superior and inferior surfaces of the two shells remains relatively constant between the collapsed and expanded configurations. In some embodiments, the angle between the superior and inferior surfaces is not the same between the collapsed and expanded configurations. Such changes in the angle between the superior and inferior surfaces may be achieved by adjusting the angles of the various angled channels of superior shell 305 and inferior shell 310.

In some embodiments, the angle between the superior and inferior surfaces in an expanded configuration is greater than about 1 degree, greater than about 3 degrees, greater than about 5 degrees, greater than about 10 degrees, greater than about 15 degrees, or greater than about 25 degrees. In some embodiments, the angle between the superior and inferior surfaces in an expanded configuration is less than about 40 degrees, less than about 35 degrees, less than about 30 degrees, less than about 25 degrees, less than about 20 degrees, or less than about 15 degrees. In some embodiments, the angle between the superior and inferior surfaces in an expanded configuration is between about 1 and about 10 degrees, between about 5 and about 15 degrees, between about 10 and about 20 degrees, between about 15 and about 25 degrees, or between about 20 and about 30 degrees.

FIG. 8 illustrates that interbody 300 contains a control assembly 400 that includes a proximal cage 405, a distal cage 410, and an adjustment screw (not shown). Similar to control assembly 200, rotation of the adjustment screw of control assembly 400 causes proximal cage 405 and distal cage 410 to translate relative to each other, which in turn causes an expansion of superior shell 305 and inferior shell 310.

As illustrated by the various embodiments, an expandable interbody according to this disclosure may exhibit little to no lordotic angle or a substantial lordotic angle. In other words, the angle between the superior surface of the superior shell and the inferior surface of the inferior shell may be roughly parallel or about 0° (as illustrated by interbody 100), or the angle may be greater than 0°, such as between about 5° and about 40° (as illustrated by interbody 300).

In some embodiments of interbody 300, the angle between the superior surface of superior shell 305 and the inferior surface of 310 is between about 4° and about 11°, between about 9° and about 16°, between about 14° and about 21°, between about 19° and about 26°, between about 24° and about 31°, between about 29° and about 36°, or between about 34° and about 41°. In some embodiments, the angle is less than about 45° and greater than about 2°, less than about 35° and greater than about 5°, less than about 30° and greater than about 10°, or less than about 25° and greater than about 15°.

In some embodiments, the initial angle (i.e., when interbody 300 is in a collapsed or unexpanded state) between the superior surface of superior shell 305 and the inferior surface of inferior shell 310 is substantially the same as the final angle (i.e., when interbody 300 is in an expanded state). In some embodiments, the initial angle and final angle are not the same. For example, control assembly 400 may be configured to interact with superior shell 305 and inferior shell 310 in a way that changes the angle of the shells as they are expanded, such as by adjusting the positions of the lateral projections and/or by adjusting the angles of the various angled channels in the shells. Similarly, control assembly 200 may be configured to interact with superior shell 105 and inferior shell 110 in a way that changes the angle of the shells as they are expanded. In such embodiments, the difference between the initial angle and the final angle may be any value between and including about 1° and about 20°. In some embodiments, the angular difference is between about 2° and about 6°, between about 5° and about 9°, between about 8° and about 12°, between about 11° and about 15°, or between about 14° and about 18°.

FIG. 9 is an exploded view of interbody 300 illustrating that, in this embodiment, control assembly 400 further includes a retention pin 420 that holds adjustment screw 415 in a fixed relationship relative to proximal cage 405. Adjustment screw 415 is inserted through a distal opening of proximal cage 205 so that the threaded portion of adjustment screw 415 extends distally of proximal cage 405 at which point retention pin 420 is inserted into proximal cage 405 and at least partially around a collar portion of adjustment screw 415 thereby allowing adjustment screw 415 to rotate. In some embodiments, retention pin 420 provides a resistance force to the rotation of adjustment screw 415 so as to limit or prevent undesired rotation of adjustment screw 415.

The threaded portion of adjustment screw 415 that extends beyond proximal cage 405 threadingly engages a threaded distal opening of distal cage 410 such that rotation of adjustment screw 415 causes distal cage 410 to move relative to proximal cage 405. In some embodiments, adjustment screw 415 is fixed relative to distal cage 410 and threadingly engages proximal cage 405. In some embodiments, adjustment screw 415 engages the respective proximal ends of the two cages rather than the respective distal ends of the two cages.

FIG. 4 illustrates that one side wall inferior shell 310 includes channels 340 and 345, one of which is distally angled (channel 345) and one of which is proximally angled (channel 340). The opposite side wall of inferior shell 310 includes channels that mirror channels 340 and 345. As will be understood by a skilled artisan, the position and angle of these channels may be adjusted to achieve different types of expansion of the interbody. For example, in some embodiments, the positions of the channels can be reversed so that the reverse translation of the cages is required to achieve expansion of the interbody. In some embodiments, the channels may be slots that extend completely through the shell.

FIG. 9 illustrates various aspects of proximal cage 405 and distal cage 410. Each cage in this illustrated embodiment has proximal and distal ends, each one of which includes an opening or bore hole that may or may not be threaded. Each cage in this embodiment also has side walls that are designed to allow proximal cage 405 and distal cage 410 to fit together and allow for translational movement between the two. Each cage also has four lateral extensions, two located superiorly and two located inferiorly. The superior lateral extensions of proximal cage 405 are designed to fit in and slide along the proximally angled channels of superior shell 305, and the superior lateral extensions of distal cage 410 are designed to fit in and slide along the distally angled channels of superior shell 305. The inferior lateral extensions of proximal cage 405 and distal cage 410 are similarly designed and configured to fit in and slide along the respective proximally and distally angled channels of inferior shell 310. Longitudinal translation of proximal cage 405 and distal cage 410 causes their various lateral extensions to slide along the angled channels and, in some embodiments, apply a force to the angled channels of superior shell 305 and inferior shell 310 to thereby cause the two shells to separate.

FIG. 4 also illustrates that proximal cage 405 and distal cage 410 each include ramped or angled surfaces at their respective distal and proximal ends. These ramped or angled surfaces are designed and configured to interact with the respective proximal and distal ramps found in superior shell 305 and inferior shell 310. Longitudinal translation of proximal cage 405 and distal cage 410 causes their various ramped surfaces to contact and, in some embodiments, apply a force to the ramped surfaces of superior shell 305 and inferior shell 310 to thereby cause the two shell pieces to separate. Contact between these various surfaces further serves to provide overall stability to interbody 300 as it is expanded and/or collapsed.

FIG. 9 illustrates that control assembly 400 includes pins 455. In some embodiments, pins 455 are replaced with rounded surfaces. Pins 455 are configured to reduce the friction between the cages and the ramped surfaces of the two shells. The material of pins 455 may be selected to have a lower coefficient of friction than the material comprising the cages. In some embodiments, the surfaces of pins 455 are treated or prepared so as to exhibit a lower coefficient of friction.

One or more of pins 455 may also be configured to slide in one or more of channels 340, 345 or the other non-illustrated channels. In such an arrangement, the one or more pins will replace the lateral extensions that otherwise would have slid along the channels.

Figure 10:
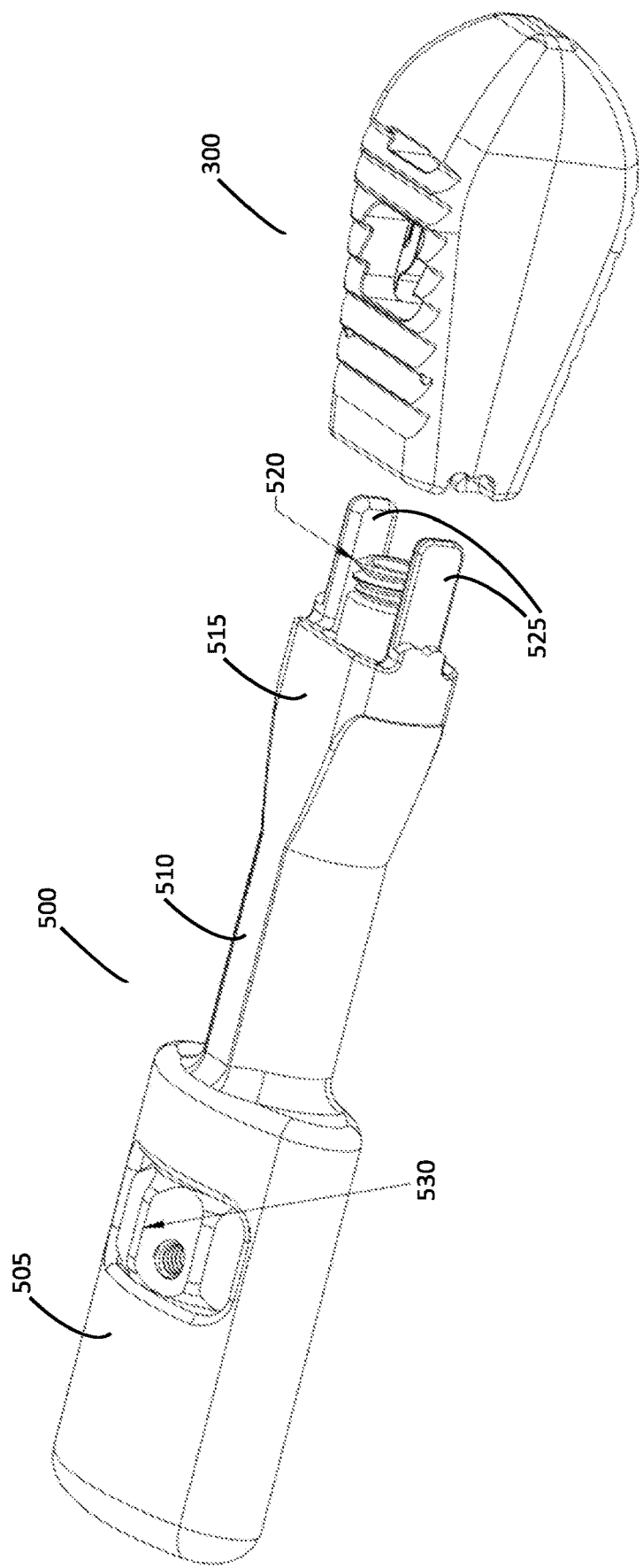
FIG. 10 is a perspective view of an inserter and the embodiment of FIG. 7.

FIG. 10 illustrates an inserter 500 that can be used with interbody 300. A similar inserter may be used with interbody 100. Inserter 500 includes a handle portion 505, an elongate portion 510, and an engagement portion 515 that further includes an engagement assembly comprising an engagement mechanism 520 and engagement prongs 525, both of which are configured to mate and engage with corresponding features on the proximal end of interbody 300. Specifically, engagement mechanism 520—in this embodiment—comprises a threaded portion that threadingly engages a threaded portion of proximal cage 405. Simultaneously, engagement prongs 425 engage depressions or cavities located at the proximal end of interbody 300, depressions or cavities that may be formed in superior shell 305 and inferior shell 310 or, in addition to the cavities in the respective shells, in cavities formed in proximal cage 405. Such a configuration allows inserter 500 to distribute an insertion or compaction force to the shell portions rather than have proximal cage 405 receive the entire insertion force.

A skilled artisan will recognize that engagement mechanism 520 represents a distal end of a lumen or cannulated structure that extends the length of inserter 500 to allow for an expansion tool (not illustrated) to be inserted through inserter 500 so as to extend into interbody 300 (or interbody 100) and engage with control assembly 400 (or control assembly 200). Rotation of such an expansion tool causes control assembly 400 to drive the expansion of interbody 300 or to collapse interbody 300. The lumen extending the length of inserter 300 also allows for the passage of bone-growth-promoting material through inserter 500 and into interbody 300 once interbody 300 has been desirably situated in the intervertebral disc space and expanded to a desirable degree.

Attachment to and detachment from interbody 300 can be achieved by rotating control knob 530, which in turn rotates attachment mechanism 520. In some embodiments, inserter 500 further includes an expansion indicator (that work in conjunction with an expansion tool discussed above) that provides information to a user regarding the degree of expansion achieved by interbody 300. This may be particularly helpful to the surgeon as the expansion may not be visible when interbody 300 (or interbody 100) has been inserted into the intervertebral space. Moreover, fluoroscopic images are not likely to provide the surgeon with precise information as to the degree of expansion achieved in situ. An expansion indicator may provide a percentage value of the expansion and/or it may provide an indication of the height achieved by the interbody. For example, if interbody 300 has been designed to achieve a final height of 10 mm when fully expanded, the expansion indicator will indicate what percentage or portion of that height that has been achieved. When the interbody is in its unexpanded state (before being inserted), the expansion indicator will show 0% expansion or 0 mm in height achieved. Assuming a final expanded height of 10 mm and an initial unexpanded height of 5 mm, when the interbody has been expanded to about 7.5 mm, the expansion indicator will show 50% expansion, and when the interbody has been expanded to about 10 mm, the expansion indicator will show 100% expansion.

Interbody 100 (and interbody 300) may be surgically implanted in a patient using any number of suitable methods. In some embodiments, a method of implanting interbody 100 includes the initial step of engaging the distal end of inserter 500 to the proximal end of proximal cage 205. This is done by bringing the engagement mechanism 520 of inserter 500 into contact with the proximal end of proximal cage 205 and rotating engagement knob 530, which in turn rotates engagement portion 520 causing the threads of engagement portion 520 to engage the threads of threaded bore 130 in proximal cage 205. Engagement knob 530 is rotated until engagement prongs 425 are fully advanced into the respective slots on the proximal end of interbody 100 formed in the proximal end of proximal cage 205 as well as in the proximal ends of the respective side walls of superior shell 105 and inferior shell 110. With inserter 500 engaged with interbody 100, an expansion tool can be inserted through inserter 500 to bring its distal end into engagement with adjustment screw 215. In some embodiments, the expansion tool is already in place in inserter 500 before inserter 500 is engaged with interbody 500.

With interbody 100 secured to inserter 500, interbody 100 is positioned in the intervertebral disc space and positioned as desired. Positioning interbody 100 in a desired location can be achieved using fluoroscopy. To this end, one or more of the components of interbody 100 can be at least partially radiopaque. In some embodiments, interbody 100 includes one or more radiopaque markers whose primary purpose is to aid in proper positioning of interbody 100 in the intervertebral disc space. In some embodiments, the expansion tool is not inserted through inserter 500 until interbody 100 has been properly positioned in the intervertebral disc space. In embodiments where interbody 100 is positioned prior to insertion of the expansion tool, the proximal end of inserter 500 can be constructed to receive and withstand hammer blows that may be required to properly position interbody 100.

With interbody 100 properly positioned, the expansion tool—which may need to be inserted through inserter 500 at this stage—is rotated to cause adjustment screw 215 to rotate, thereby causing control assembly 200 to drive the expansion of interbody 100, which is achieved when proximal cage 205 and distal cage 210 are moved longitudinally relative to each other. Movement of the two cages applies an outward pressure on superior shell 105 and inferior shell 110. In some embodiments, this outward pressure comes from lateral extensions 225 sliding along angled channels 140 and 145. In some embodiments, this outward pressure comes from the tapered or angled surfaces of proximal cage 205 and distal cage 210 that press against sloped surfaces on the interior of superior shell 105 and inferior shell 110. In some embodiments, this outward pressure comes from a combination of these structural interactions.

Interbody 100 is expanded by continuing to rotate the expansion tool until a desired amount of expansion is achieved. The amount of expansion can be observed using an expansion indicator or by using fluoroscopy.

Once the desired amount of expansion is achieved, the expansion tool is removed from inserter 500. In some embodiments, biologics or materials that promote bone growth are then injected into interbody 100 by injecting them through the cannulated structure of inserter 500. In some embodiment, such materials are injected into interbody 100 or the space surrounding interbody 100 after the inserter has been disengaged from interbody 100. Disengagement is achieved by turning engagement knob 530 until the distal tip of inserter 500 can be freely withdrawn from the surgical space without affecting the positioning of interbody 100.

Yet another embodiment of the present disclosure—although not illustrated—utilizes many of the same components and configures of the other embodiments; however, the distal opening of the proximal cage is threaded and threadingly engages the exterior threads of the adjustment screw. Moreover, in some embodiments, the adjustment screw is a twin screw comprising a proximal screw having a threaded bore open at the distal end of the screw with a distal screw threadingly engaged in the threaded bore of the proximal screw, such that rotation of the proximal screw causes the distal screw—which is prevented from rotating by engagement with the distal cage—to translate to a greater extent than would be achieved by the proximal screw alone. In such an embodiment, the distal end of the distal screw engages with the distal cage in a manner than rotationally fixes the distal screw, which can be achieved by simply fitting the non-circular distal end in a non-circular bore in the distal cage and/or by securing the distal end of the distal screw to the distal cage with a cross pin or other means that cause the distal cage to not only translate in an expansive manner but also in reverse so as to collapse the interbody.

Although there may be any number of advantages to using a twin screw as described herein, the authors of this disclosure have found that such a configuration reduces friction in the interbody allowing less torque to be used to expand the interbody that is under pressure in the intervertebral disc space.

EMBODIMENTS

The following embodiments are provided as examples only of specific configurations, materials, arrangements, etc. contemplated by the authors of this disclosure:

Embodiment 1

An Expandable Interbody Comprising:
a superior shell having a proximal end and a distal end, the superior shell defining a superior surface extending from the proximal end to the distal end configured to engage an inferior surface of a first vertebral body, the superior shell having two side walls each wall having a proximally angled channel and a distally angled channel;
an inferior shell having a proximal end and a distal end, the inferior shell defining an inferior surface configured to engage a superior surface of a second vertebral body, the inferior shell having two side walls each wall having a proximally angled channel and a distally angled channel; and a control member comprising interlocking proximal and distal cages and an adjustment screw defining a longitudinal axis, the adjustment screw configured to engage with the proximal and distal cages;

wherein the proximal cage comprises a pair of superior lateral projections and a pair of inferior lateral projections respectively configured to engage with the pairs of proximally angled channels of the superior and inferior shells;

wherein the distal cage comprises a pair of superior lateral projections and a pair of inferior lateral projections respectively configured to engage with the pairs of distally angled channels of the superior and inferior shells;

wherein rotation of the adjustment screw causes the distal cage to move longitudinally relative to the proximal cage, which in turn causes the interbody to expand or contract in a direction transverse to the longitudinal axis.

Embodiment 2

An Expandable Interbody Comprising:

a superior shell having a proximal end and a distal end, the superior shell defining a superior surface extending from the proximal end to the distal end configured to engage an inferior surface of a first vertebral body, the superior shell having two side walls, at least one wall having at least one angled channel;

an inferior shell having a proximal end and a distal end, the inferior shell defining an inferior surface configured to engage a superior surface of a second vertebral body, the inferior shell having two side walls, at least one wall having at least one angled channel; and a control member comprising interlocking proximal and distal cages and an adjustment screw defining a longitudinal axis, the adjustment screw configured to engage with the proximal and distal cages;

wherein the proximal cage comprises at least one superior lateral projection and at least one inferior lateral projection, each lateral projection configured to engage with one of the at least one angled channel of the superior and inferior shells;

wherein the distal cage comprises a at least one superior lateral projection and at least one inferior lateral projection, each lateral projection configured to engage with one of the at least one angled channel of the superior and inferior shells, wherein rotation of the adjustment screw causes the distal cage to move longitudinally relative to the proximal cage, which in turn causes the interbody to expand or contract in a direction transverse to the longitudinal axis.

Embodiment 3

The expandable interbody of embodiment 1 or 2, wherein the superior and inferior shells each further comprise distal and proximal angled surfaces, wherein the distal and proximal cages each further comprise superior and inferior angled surfaces that engage with the angled surfaces of the superior and inferior shells.

Embodiment 4

The expandable interbody of embodiment 3, wherein at least one of the angled surfaces of the proximal and distal cages defines a rounded surface or cylindrical-shaped surface so as to achieve a linear point of contact between it and the corresponding angled surface of the superior and/or inferior shell.

Embodiment 5

The expandable interbody of embodiment 4, wherein the cylindrical-shaped surface comprises a pin.

Embodiment 6

The expandable interbody of embodiment 5, wherein the pin comprises a material distinct from that of the cage to which it is secured.

Embodiment 7

The expandable interbody of embodiment 6, wherein the material of the pin is selected to achieve a lower coefficient of friction between it and the ramps of the superior and/or inferior shells than would be achieved if the material of the pin were identical to that of the cage.

Embodiment 8

The expandable interbody of embodiment 1, 2, 3, 4, 5, 6, or 7, wherein one or more of the lateral projections comprises a pin secured to the proximal and/or distal cage, at least one end of the pin is configured to slide along the appropriate angled channel.

Embodiment 9

The expandable interbody of embodiment 8, wherein the pin comprises a material distinct from that of the cage to which it is secured.

Embodiment 10

The expandable interbody of embodiment 9, wherein the material of the pin is selected to achieve a lower coefficient of friction between it and the channels of the superior and/or inferior shells than would be achieved if the material of the pin were identical to that of the cage.

Embodiment 11

The expandable interbody of embodiment 1, 2, 3, 4, 5, 6, 7, 8, 9, or 10, wherein the adjustment screw threadingly engages with the distal cage and is in a fixed longitudinal orientation relative to the proximal cage.

Embodiment 12

The expandable interbody of embodiment 1, 2, 3, 4, 5, 6, 7, 8, 9, or 10, wherein the adjustment screw threadingly engages with the proximal cage and is in a fixed longitudinal orientation relative to the distal cage.

Embodiment 13

The expandable interbody of embodiment 1, 2, 3, 4, 5, 6, 7, 8, 9, or 10, wherein the adjustment screw threadingly engages with both the proximal cage and the distal cage.

Embodiment 14

The expandable interbody of embodiment 1, 2, 3, 4, 5, 6, 7, 8, 9, 10, 11, 12, or 13, wherein the adjustment screw comprises a twin screw having a proximal screw and a distal screw, the proximal screw having a threaded bore open at its distal end and configured to threadingly receive the distal screw.

Embodiment 15

The expandable interbody of embodiment 3, 4, 5, 6, 7, 8, 9, 10, 11, 12, 13, or 14, wherein the relative movement between the distal and proximal cages is translated to the superior and inferior cages by the force applied by the angled surfaces of the proximal and distal cages on the angled surfaces of the superior and inferior shells.

Embodiment 16

The expandable interbody of embodiment 1, 2, 3, 4, 5, 6, 7, 8, 9, 10, 11, 12, 13, 14, or 15, wherein the relative movement between the distal and proximal cages is translated to the superior and inferior cages by the interaction between the lateral projections and lateral channels.

Embodiment 17

The expandable interbody of embodiment 1, 2, 3, 4, 5, 6, 7, 8, 9, 10, 11, 12, 13, 14, 15, or 16, wherein at least one of the superior and inferior shells is curved at the distal end.

Embodiment 18

The expandable interbody of embodiment 1, 2, 3, 4, 5, 6, 7, 8, 9, 10, 11, 12, 13, 14, 15, 16, or 17, wherein both the superior and inferior shells are curved toward each other at their respective distal ends so as to form a bullet-like nose shape that at least partially encloses the distal end of the interbody when in a collapsed configuration.

Embodiment 19

The expandable interbody of embodiment 1, 2, 3, 4, 5, 6, 7, 8, 9, 10, 11, 12, 13, 14, 15, 16, 17, or 18, wherein—when in an expanded configuration—the superior shell, inferior shell, proximal cage, and distal cage each comprise openings therethrough extending from the superior surface of the superior shell to the inferior surface of the inferior shell so as to define a channel for bone growth.

Embodiment 20

The expandable interbody of embodiment 1, 2, 3, 4, 5, 6, 7, 8, 9, 10, 11, 12, 13, 14, 15, 16, 17, 18, or 19, wherein the interbody comprises a titanium alloy.

Embodiment 21

The expandable interbody of embodiment 1, 2, 3, 4, 5, 6, 7, 8, 9, 10, 11, 12, 13, 14, 15, 16, 17, 18, or 19, wherein the interbody consists of a titanium alloy.

Embodiment 22

The expandable interbody of embodiment 1, 2, 3, 4, 5, 6, 7, 8, 9, 10, 11, 12, 13, 14, 15, 16, 17, 18, 19, 20, or 21, wherein at least one of the superior shell, inferior shell, proximal cage, distal cage, and adjustment screw comprises a porous material.

Embodiment 23

The expandable interbody of embodiment 22, wherein the porous material comprises layers of porous sheets that have been diffusion-bonded to form a uniform material.

Embodiment 24

The expandable interbody of embodiment 1, 2, 3, 4, 5, 6, 7, 8, 9, 10, 11, 12, 13, 14, 15, 16, 17, 18, 19, 20, 21, 22, or 23, wherein the superior surface defines a first plane and the inferior surface defines a second plane that is substantially parallel to the first plane when the interbody is in a collapsed configuration.

Embodiment 25

The expandable interbody of embodiment 24, wherein the first plane is substantially parallel to the second plane when the interbody is in an expanded configuration.

Embodiment 26

The expandable interbody of embodiment 24, wherein the first plane is substantially not parallel to the second plane when the interbody is in an expanded configuration.

Embodiment 27

The expandable interbody of embodiment 1, 2, 3, 4, 5, 6, 7, 8, 9, 10, 11, 12, 13, 14, 15, 16, 17, 18, 19, 20, 21, 22, or 23, wherein the superior surface defines a first plane and the inferior surface defines a second plane, and wherein the first and second planes are substantially parallel to each when the interbody is in a collapsed configuration and when the interbody is in the expanded configuration.

Embodiment 28

The expandable interbody of embodiment 1, 2, 3, 4, 5, 6, 7, 8, 9, 10, 11, 12, 13, 14, 15, 16, 17, 18, 19, 20, 21, 22, 23, 24, 25, 26, or 27, wherein the superior and inferior shells are configured to at least partially nest within each other when the interbody is in a collapsed configuration.

Embodiment 29

The expandable interbody of embodiment 1, 2, 3, 4, 5, 6, 7, 8, 9, 10, 11, 12, 13, 14, 15, 16, 17, 18, 19, 20, 21, 22, 23, 24, 25, 26, 27, or 28, wherein the proximal and distal cages further comprise side walls configured to contact respective inside surfaces of the side walls of the superior and inferior shells so as to provide structural support to the interbody.

Embodiment 30

The expandable interbody of embodiment 1, 2, 3, 4, 5, 6, 7, 8, 9, 10, 11, 12, 13, 14, 15, 16, 17, 18, 19, 20, 21, 22, 23, 24, 25, 26, 27, 28, or 29, wherein the edge of the side wall of either the superior shell or the inferior shell comprises projections and the edge of the side wall of the other shell comprises depressions configured to receive the projections so as to provide the interbody with greater structural integrity when the interbody is in a collapsed configuration.

Embodiment 31

The expandable interbody of embodiment 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30, wherein the superior surface of the superior shell and/or the inferior surface of the inferior shell further comprise a cutout or a depression containing a layer of a porous material.

Embodiment 32

The expandable interbody of embodiment 31, wherein the layer of porous material comprises one or more diffusion-bonded sheets of porous titanium alloy.

Embodiment 33

The expandable interbody of embodiment 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, or 32, wherein at least one of the proximal and distal cages includes one or more projections extending beyond the superior and/or inferior surfaces so as to provide greater stability to the superior and/or inferior shell when the expandable interbody is in an expanded configuration.

Embodiment 34

The expandable interbody of embodiment 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, or 32, wherein the lateral projections of the proximal and distal cages extend through the superior and inferior surfaces when the interbody is in an expanded configuration.

Embodiment 35

The expandable interbody of embodiment 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, or 34, wherein the proximal end of the proximal cage includes an opening for receiving a bone-growth-promoting material.

Embodiment 36

The expandable interbody of embodiment 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, or 35, wherein the proximal ends of the superior and inferior shells include inserter engagement surfaces configured to engage an inserter.

Embodiment 37

A method of implanting the expandable interbody of embodiment 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, or 36, the method comprising:
- with an inserter, positioning the interbody in a collapsed configuration in an intervertebral disc space;
- expanding the interbody by rotating a control handle on the inserter that in turn rotates the adjustment screw; and
- releasing the expanded interbody from the inserter;

Embodiment 38

The method of embodiment 37 further comprising, before releasing the expanded interbody from the inserter, injecting a material that promotes bone growth into the interbody through an opening in the proximal end of the interbody.

While particular embodiments have been illustrated and described herein, it should be understood that various other changes and modifications may be made without departing from the spirit and scope of the claimed subject matter. Moreover, although various aspects of the claimed subject matter have been described herein, such aspects need not be utilized in combination.

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the embodiments of the present disclosure. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the present disclosure are approximations, the numerical values set forth in the specific examples are reported as precisely as possible. Any numerical value, however, inherently contains certain errors necessarily resulting from the standard deviation found in their respective testing measurements. In one embodiment, the terms "about" and "approximately" refer to numerical parameters within 10% of the indicated range.

The terms "a," "an," "the," and similar referents used in the context of describing the embodiments of the present disclosure (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate the embodiments of the present disclosure and does not pose a limitation on the scope of the present disclosure. No language in the specification should be construed as indicating any non-claimed element essential to the practice of the embodiments of the present disclosure.

Groupings of alternative elements or embodiments disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Certain embodiments are described herein, including the best mode known to the author(s) of this disclosure for carrying out the embodiments of the present disclosure. Of course, variations on these described embodiments will become apparent to those of ordinary skill in the art upon reading the foregoing description. The author(s) of this disclosure expects skilled artisans to employ such variations as appropriate, and the author(s) intends for the embodiments of the present disclosure to be practiced otherwise than specifically described herein. Accordingly, this disclosure includes all modifications and equivalents of the subject matter recited in the claims appended hereto as permitted by applicable law. Moreover, any combination of the above-described elements in all possible variations thereof is encompassed by the present disclosure unless otherwise indicated herein or otherwise clearly contradicted by context.

Specific embodiments disclosed herein may be further limited in the claims using consisting of or consisting essentially of language. When used in the claims, whether as filed or added per amendment, the transition term "consisting of" excludes any element, step, or ingredient not specified in the claims. The transition term "consisting essentially of" limits the scope of a claim to the specified materials or steps and those that do not materially affect the basic and novel characteristic(s). Embodiments of this disclosure so claimed are inherently or expressly described and enabled herein.

Furthermore, if any references have been made to patents and printed publications throughout this disclosure, each of these references and printed publications are individually incorporated herein by reference in their entirety.

In closing, it is to be understood that the embodiments disclosed herein are illustrative of the principles of the present disclosure. Other modifications that may be employed are within the scope of this disclosure. Thus, by way of example, but not of limitation, alternative configurations of the embodiments of the present disclosure may be utilized in accordance with the teachings herein. Accordingly, the present disclosure is not limited to that precisely as shown and described.

The invention claimed is:

1. An expandable interbody comprising:
    a superior shell having two side walls, each of the superior shell side walls having at least one angled channel;
    an inferior shell having two side walls, each of the inferior superior shell side walls having at least one angled channel; and
    a control member comprising interlocking proximal and distal cages and an adjustment screw defining a longitudinal axis, the adjustment screw configured to engage with the proximal and distal cages;
    wherein the proximal cage comprises at least one superior lateral projection and at least one inferior lateral projection, each lateral projection of the proximal cage configured to engage with one of the angled channels of the superior and inferior shells;
    wherein the distal cage comprises at least one superior lateral projection and at least one inferior lateral projection, each lateral projection of the distal cage configured to engage with one of the angled channels of the superior and inferior shells; and
    wherein rotation of the adjustment screw causes the distal cage to move longitudinally relative to the proximal cage, which in turn causes the expandable interbody to expand or contract in a direction transverse to the longitudinal axis.

2. The expandable interbody of claim 1, wherein the superior and inferior shells each further comprise distal and proximal angled surfaces, and wherein the distal and proximal cages each further comprise superior and inferior angled surfaces that respectively engage with the distal and proximal angled surfaces of the superior and inferior shells.

3. The expandable interbody of claim 2, wherein at least one of the superior and inferior angled surfaces of the proximal and distal cages defines a rounded surface or a cylindrical-shaped surface so as to achieve a linear point of contact between it and the corresponding distal and proximal angled surface of the superior and/or inferior shell.

4. The expandable interbody of claim 1, wherein the adjustment screw threadingly engages with the distal cage and is in a fixed longitudinal orientation relative to the proximal cage.

5. The expandable interbody of claim 1, wherein the adjustment screw threadingly engages with the proximal cage and is in a fixed longitudinal orientation relative to the distal cage.

6. The expandable interbody of claim 1, wherein the adjustment screw threadingly engages with both the proximal cage and the distal cage.

7. The expandable interbody of claim 1, wherein the adjustment screw comprises a twin screw having a proximal screw and a distal screw, the proximal screw having a threaded bore open at its distal end and configured to threadingly receive the distal screw.

8. The expandable interbody of claim 1, wherein both the superior and inferior shells are curved toward each other at their respective distal ends so as to form a bullet-like nose shape that at least partially encloses a distal end of the expandable interbody when in a collapsed configuration.

9. The expandable interbody of claim 1, wherein when the expandable interbody is in an expanded configuration the superior shell, the inferior shell, the proximal cage, and the distal cage each comprise openings therethrough extending from the superior surface of the superior shell to the inferior surface of the inferior shell so as to define a through-channel for bone growth.

10. The expandable interbody of claim 1, wherein at least one of the superior shell, the inferior shell, the proximal cage, the distal cage, and the adjustment screw comprises a porous material.

11. The expandable interbody of claim 10, wherein the porous material comprises layers of porous sheets that have been diffusion-bonded to form a uniform material.

12. The expandable interbody of claim 1, wherein the superior surface defines a first plane and the inferior surface defines a second plane that is substantially parallel to the first plane when the expandable interbody is in a collapsed configuration.

13. The expandable interbody of claim 12, wherein the first plane is substantially parallel to the second plane when the expandable interbody is in an expanded configuration.

14. The expandable interbody of claim 12, wherein the first plane is not parallel to the second plane when the expandable interbody is in an expanded configuration.

15. An expandable interbody comprising:
    a superior shell having two side walls, each of the superior shell side walls having a plurality of angled channels;
    an inferior shell having two side walls, each of the inferior shell side walls having a plurality of angled channels; and
    a control member comprising interlocking proximal and distal cages and an adjustment screw defining a longitudinal axis, the adjustment screw configured to engage with the proximal and distal cages;
    wherein the proximal cage comprises a plurality of superior lateral projections and a plurality of inferior lateral projections, each lateral projection of the proximal cage configured to engage with a respective one of the angled channels of the superior and inferior shells;

wherein the distal cage comprises a plurality of superior lateral projections and a plurality of inferior lateral projections, each lateral projection of the distal cage configured to engage with a respective one of the angled channels of the superior and inferior shells; and wherein rotation of the adjustment screw causes the distal cage to move longitudinally relative to the proximal cage, which in turn causes the expandable interbody to expand or contract in a direction transverse to the longitudinal axis.

16. The expandable interbody of claim 15, wherein both the superior and inferior shells are curved toward each other at their respective distal ends so as to form a bullet-like nose shape that at least partially encloses a distal end of the expandable interbody when in a collapsed configuration.

17. The expandable interbody of claim 15, wherein at least one of the superior shell, the inferior shell, the proximal cage, the distal cage, and the adjustment screw comprises a porous material.

18. The expandable interbody of claim 17, wherein the porous material comprises layers of porous sheets that have been diffusion-bonded to form a uniform material.

19. The expandable interbody of claim 15, wherein the adjustment screw comprises a twin screw having a proximal screw and a distal screw, the proximal screw having a threaded bore open at its distal end and configured to threadingly receive the distal screw.

\* \* \* \* \*